United States Patent [19]

Woodle

[11] 4,137,753
[45] Feb. 6, 1979

[54] METHOD AND APPARATUS FOR MONITORING THE PARAFFINICITY CHARACTERIZATION OF HYDROCARBON MIXTURES

[75] Inventor: Robert A. Woodle, Nederland, Tex.

[73] Assignee: Texaco Inc., New York, N.Y.

[21] Appl. No.: 816,847

[22] Filed: Jul. 18, 1977

[51] Int. Cl.$^2$ .................. G01N 11/00; G01N 33/26
[52] U.S. Cl. ...................... 73/53; 73/32 R; 73/54
[58] Field of Search ..................... 73/32 R, 53, 54

[56] References Cited

U.S. PATENT DOCUMENTS 3,557,609  1/1971  Woodle ........................... 73/53

Primary Examiner—James J. Gill
Attorney, Agent, or Firm—Thomas H. Whaley; Carl G. Ries; Henry C. Dearborn

[57] ABSTRACT

A method for determining the Watson-Nelson characterization factor of hydrocarbons wherein the absolute viscosity and specific gravity are sensed providing first and second signals, respectively, corresponding to the absolute viscosity and specific gravity. The signals are then combined in accordance with the following equation:

$$K = A + B/S_2 + C \ln \ln (V/S_1)$$

where:
$K$ = the Watson-Nelson characterization factor of the hydrocarbon mixture;
$V$ = the absolute viscosity of the hydrocarbon mixture;
$S_1$ = the specific gravity of the hydrocarbon mixture;
$S_2$ = the specific gravity of the hydrocarbon mixture adjusted to 60° F; and
$A$, $B$ and $C$ are predetermined constants.

1 Claim, 6 Drawing Figures

METHOD AND APPARATUS FOR MONITORING THE PARAFFINICITY CHARACTERIZATION OF HYDROCARBON MIXTURES

BACKGROUND OF THE INVENTION

1. Field of the Invention

This invention relates to methods and apparatus for the characterization of a hydrocarbon mixture in accordance with its paraffinicity. More specifically, this invention relates to an improved method and apparatus for monitoring the Watson-Nelson characterization factor of hydrocarbon mixtures.

2. Description of the Prior Art

As was previously explained in my prior U.S. Pat. No. 3,557,609, the Watson-Nelson characterization factor, K, is a very useful tool for describing by one numerical quantity the relative paraffinicity of a petroleum crude oil or a fraction thereof. It was first described in the literature in 1933 in Ind. Eng. Chem., Vol. 25, page 880, by its originators, who observed an empirical relationship between specific gravity and average boiling point of different boiling range fractions from a given crude oil. This observation led to the development of the equation:

$$K = \frac{\sqrt[3]{T_B}}{s} \qquad (1)$$

wherein:
K = Watson-Nelson characterization factor;
$T_B$ = average boiling point, °R; and
s = specific gravity at 60° F.

In general, the characterization factor is useful because it correlates with the average hydrocarbon type analysis, or quality of an oil. Thus, for example, the characterization factor can be used to distinguish a heavy oil of one crude from a similar oil of a different crude, a refined oil from the parent charge stock, and a higher VI (viscosity index) refined oil from a lower VI refined oil, both prepared from the same parent oil. Accordingly, it is extremely useful to continuously monitor the characterization factor of refinery process streams to distinguish among products, and to detect changes which occur during processing. For example, changes which can be detected include changes in crude oil quality or composition supplied to crude stills, changes in charge stock quality to refining or deasphalting processes, and changes in product oil quality from refining or deasphalting processes. Thus, the characterization factor can be used as the basis for control of various refinery operations.

Given the required data, i.e., the average boiling point and the specific gravity, it is relatively easy to calculate K in accordance with the above equation. However, the average boiling point is not a property that lends itself readily to continuous on-stream measurements. In fact, for very heavy oils, it is very difficult and sometimes impossible, to determine the average boiling point of the oil.

Consequently, and in accordance with the invention disclosed herein, I have provided an improved capability for the continuous on-stream determination of the Watson-Nelson characterization factor whereby various petroleum refining processes can be monitored or controlled automatically, or by computer, resulting in improved product quality and economy.

SUMMARY OF THE INVENTION

Briefly, the invention deals with a method for generating a signal which is representatives of the Watson-Nelson characterization factor of a hydrocarbon mixture. It comprises the steps which follow. One step is that of sensing a physical property of said hydrocarbon mixture representative of the absolute viscosity thereof and providing a first signal representative of said absolute viscosity. Another step is that of sensing a physical property of said hydrocarbon mixture representative of the specific gravity thereof and providing a second signal representative of said specific gravity. And, another step is that of deriving a third signal representative of said characterization factor by combining said first and second signals in accordance with an empirical relationship relating said absolute viscosity and said specific gravity with said characterization factor. The general form of said relationship is substantially in accordance with the following equation:

$$K = A + B/S_2 + C \ln \ln (V/S_1)$$

where:
K = the Watson-Nelson characterization factor of the hydrocarbon mixture,
V = the absolute viscosity of said hydrocarbon mixture,
$S_1$ = the specific gravity at the temperature of the hydrocarbon mixture,
$S_2$ = the specific gravity of the hydrocarbon mixture adjusted to sixty degrees F., and
A, B, and C are predetermined constants related to the temperature of said hydrocarbon mixture.

In accordance with another aspect of the invention there is provided apparatus in combination for monitoring the Watson-Nelson characterization factor of a hydrocarbon mixture. The apparatus includes first means for sensing the absolute viscosity of the mixture and for providing a first signal representative thereof, and second means for sensing the specific gravity of the mixture and for providing a second signal representative thereof. The apparatus further includes signal combining means, including computation elements, responsive to said first and second signals for providing a third signal representative of the characterization factor in accordance with an empirical relationship relating the absolute viscosity and the specific gravity with said characterization factor. Such empirical relationship is that set forth above.

In view of the foregoing it is an object of the invention to provide an improved method for monitoring the Watson-Nelson characterization factor of hydrocarbon mixtures.

Another object of the invention is to provide a simplified method for monitoring the Watson-Nelson characterization factor of hydrocarbon mixtures suitable for on-stream use.

Another object of the invention is to provide a simplified method for monitoring the Watson-Nelson characterization factor by monitoring the absolute viscosity and specific gravity of the mixture and by relating said characterization factor to the monitored viscosity and gravity.

Another object of the invention is to provide embodiments of apparatus to fulfill the aforementioned objectives.

BRIEF DESCRIPTION OF THE DRAWINGS

The foregoing and other objects and benefits of the invention will be more fully set forth below in connection with the best mode contemplated by the inventor of carrying out the invention, and in connection with which there are illustrations provided in the drawings, wherein.

DESCRIPTION OF THE PREFERRED EMBODIMENTS

As explained in my aforementioned prior U.S. Pat. No. 3,557,609 oils having the same viscosity and density have the same Watson-Nelson characterization factor K. In the analysis and correlation of empirical data of viscosity and density, and characterization factor computed in accordance with equation (1) above, I have learned that the Watson-Nelson characterization factor can be mathematically expressed in terms of the specific gravity and absolute viscosity of the hydrocarbon mixture. There were tables shown in my prior patent which were abbreviated examples of data which supported the foregoing conclusion. Data at intermediate points and at intermediate temperatures exhibited the same trends as the data shown in those tables.

Since density and viscosity vary with temperature the foregoing tables of data are provided with respect to various temperatures to illustrate the variations of the data which can be expected with variations of temperature. However, a given hydrocarbon mixture having a characterization factor determined at any given temperature will have the same, or nearly the same, characterization factor when determined at any other temperature.

I have now discovered that the following equation simplifies the steps necessary to determine the characterization factor in relation to the specific gravity and absolute viscosity of the hydrocarbon mixture:

$$K = A + B/S_2 + C \ln \ln (V/S_1) \quad (2)$$

where:
 $K$ = the Watson-Nelson characterization factor of the hydrocarbon mixture;
 $V$ = the absolute viscosity, centipoises, at the temperature of the hydrocarbon mixture;
 $S_1$ = the specific gravity of the hydrocarbon mixture at the temperature thereof;
 $S_2$ = the specific gravity of the hydrocarbon mixture adjusted to 60° F.; and
 A, B, and C are constants whose values depend on the mixture temperature.

One simple manner of obtaining on-stream density and viscosity information, useable in connection with refinery processes, is to use on-stream instrumentation available in the prior art for measuring specific gravity and absolute viscosity. Then, to obtain the value of $S_2$ from $S_1$ the following equation is used.

$$S_2 = R + WS_1 \quad (3)$$

where:
 R and W are constants related to the mixture temperature.

The purpose of equation (3) above is to convert the measured specific gravity to a specific gravity at the standard temperature of 60° F. Since the variation of specific gravity with temperature is far less than the variation of viscosity with temperature, the use of equation (3) can be omitted with some compromise in accuracy. Its use, however, is preferred. Also, for best accuracy it is preferred that the specific gravity and viscosity be measured at the same, or near same, stream temperatures.

Figure 4:
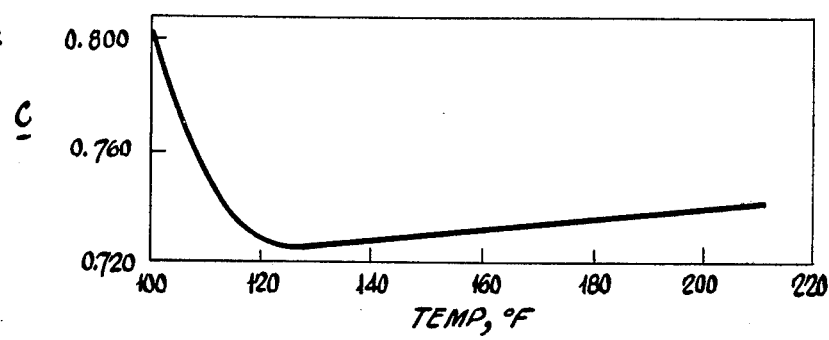
Figure 5:
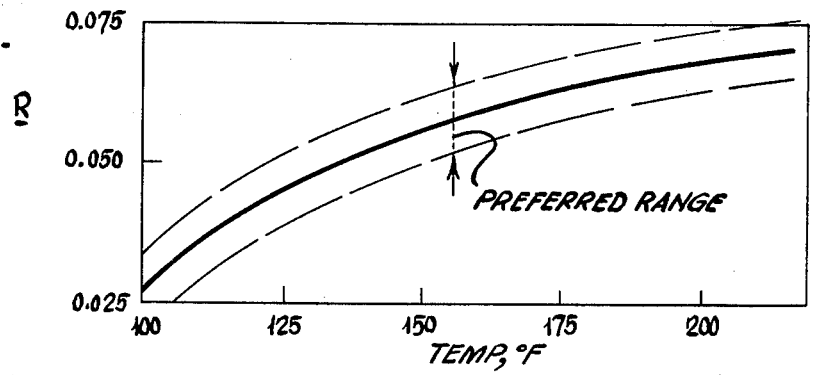
Figure 6:
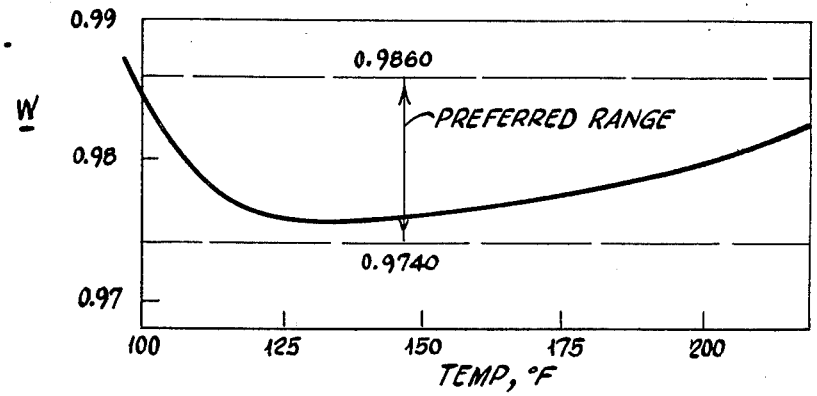

The numeric value of the constants A, B, and C in equation (2) depend upon the stream temperature. I have determined these values empirically and they are illustrated as functions of temperature in FIGS. 2, 3 and 4, respectively. Also, FIGS. 5 and 6 illustrate the values of R and W as functions of temperature.

There are three steam temperatures, among others, which are convenient in connection with many petroleum refining processes. For these temperatures I have abstracted from the data of the curves of FIGS. 2 through 6 the following table.

TABLE I

|   | 100° F | | | 122° F | | |
|---|---|---|---|---|---|---|
|   | LOW | HIGH | PRE-FERRED | LOW | HIGH | PRE-FERRED |
| A | −1.23 | −2.87 | −2.15 | −1.03 | −2.48 | −1.81 |
| B | 10.68 | 12.45 | 11.67 | 10.75 | 12.31 | 11.59 |
| C | 0.628 | 0.930 | 0.802 | 0.660 | 0.790 | 0.724 |
| R | 0.020 | 0.035 | 0.0279 | 0.032 | 0.050 | 0.0427 |
| W | 0.974 | 0.986 | 0.9845 | 0.974 | 0.986 | 0.9759 |
|   | 210° F | | | | | |
| A | −1.14 | −1.80 | −1.53 | | | |
| B | 11.32 | 12.03 | 11.74 | | | |
| C | 0.644 | 0.814 | 0.739 | | | |
| R | 0.063 | 0.075 | 0.0687 | | | |
| W | 0.974 | 0.986 | 0.980 | | | |

The preferred values are those values most likely to produce the most accurate results. The low and high values define the ranges in which acceptable accuracies result and which include the uncertainties in the empirical determination of the quantities.

Figure 1:
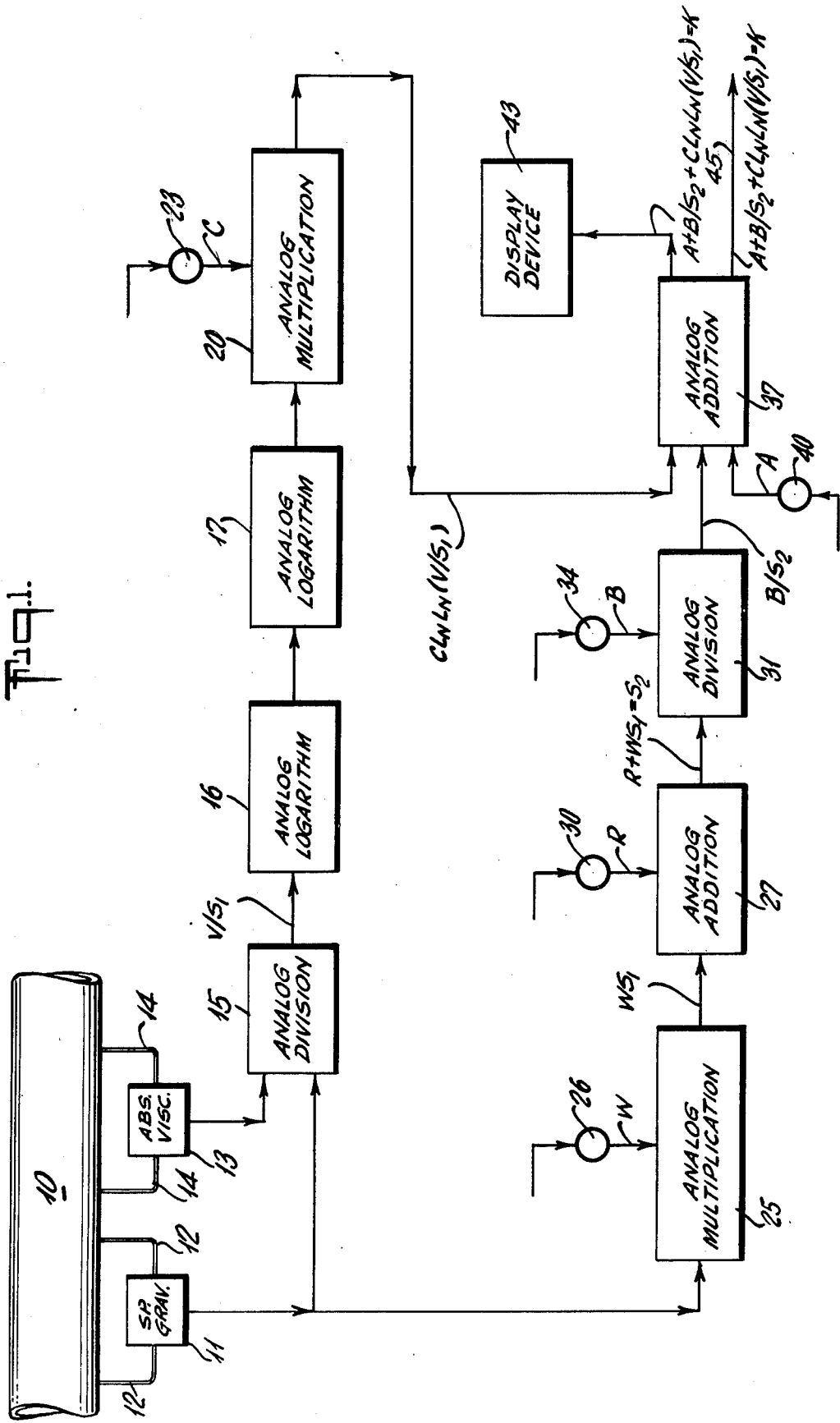
FIG. 1 is a schematic block diagram illustrating an example of a system which can be used to practice the invention for continuously monitoring the Watson-Nelson characterization factor of a hydrocarbon stream in a simplified manner.

Referring now to FIG. 1, which is a block diagram schematic illustrating an example of a system which can be used to practice the invention, there is shown a conduit 10 carrying a typical refinery process hydrocarbon stream, such as a petroleum crude, or petroleum fraction. There is connected to the conduit 10 a density sensing instrument 11 which receives a small side stream of the hydrocarbon mixture through a conduit 12. The side stream is in turn returned to the conduit 10 after passing through the density sensing instrument. The instrument 11 is of the vibrating density cell type which includes output electronics for providing a signal corresponding to the specific gravity of the sampled side stream. Also connected to the conduit 10 is a viscosity sensing instrument 13, which similarly receives a small side stream of the hydrocarbon mixtures through a conduit 14, which is in turn returned to the conduit 10 after passing through the latter instrument. The viscosity of the sampled side stream. To provide the above signals suitable measuring instruments have been found to be the Dynatrol CL-10TY Series density cell and the Dynatrol CL-10RV Series viscosity detector. Both instruments are manufactured by Automation Products, Inc., Houston, Texas.

The specific gravity and absolute viscosity signals, from the sensors 11, 13 are carried by suitable signal carrying means to a conventional analog division device 15 which divides the latter signal by the former and provides an analog output signal corresponding to the quotient, namely $V/S_1$. A suitable analog device which can be used to perform the division is that manufactured by Electronic Associates Inc., Long Branch, New Jersey, under the designation Pace PC-12 Quarter Square Multiplier, Type 7.081. The quotient signal, from the analog division device 15, is carried to a pair of conventional analog logarithmic devices 16 and 17 which provide an output signal from device 17 corresponding to the logarithm of the logarithm of the input signal. The output signal from the device 17 is carried to one input of a conventional analog multiplication device 20, which multiplies the logarithm of the logarithm of the signal representing $V/S_1$ by a signal representing the constant C in equation (2). This constant is represented by a setting on a potentiometer 23.

The specific gravity signal, from the sensing instrument 11, is also carried to a conventional analog multiplication device 25, which multiplies the specific gravity signal by the constant W which is represented by a setting on a potentiometer 26. Device 25 provides an output signal corresponding to this product. This analog multiplication device 25, like the foregoing device 20, can be a simple d.c. amplifier incorporating a manually adjustable gain feature such as a potentiometer in its feedback circuit. By manual operation of such a potentiometer the multiplication device can be adjusted to apply the proper value of the constant W or the constant C, in each case. The constant W is selected from the curve of FIG. 6.

The product signal, $WS_1$, from the multiplication device 25 is carried to a conventional analog addition device 27 which adds to this product signal the constant R. The value R which is selected from the curve of FIG. 5 is represented by the setting of a potentiometer 30. It can be seen that the sum signal provided by the analog addition device 27 corresponds to the specific gravity of the hydrocarbon mixture corrected to a standard temperature of 60° F. The devices 25 and 27 can be omitted if one is prepared to accept a compromise in the accuracy of the system, by not correcting the specific gravity to the standard temperature, or, if the temperature of the hydrocarbon mixture is maintained in the vicinity of 60° F.

Figure 3:
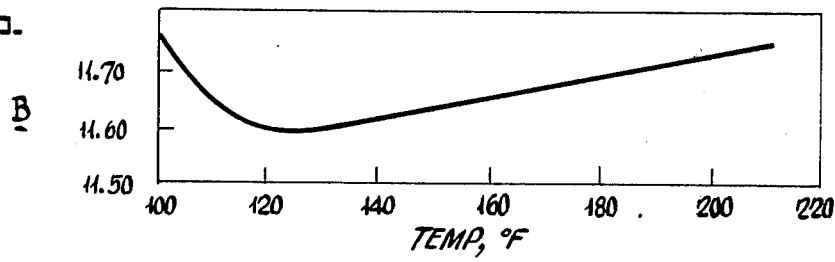

The specific gravity signal $S_2$ is carried from the analog addition device 27 to a conventional analog division device 31 which divides the constant B by the specific gravity signal $S_2$. The constant B which is selected from the curve of FIG. 3, is represented by a setting on a potentiometer 34. The quotient signal, $B/S_2$, is carried to another analog addition device 37. The analog addition device 37 sums three input signals and provides an output signal corresponding to this sum. A suitable addition device that can be used for this purpose is manufactured by Electronics Associates Inc., Long Branch, New Jersey, under the designation of a Pace PC-12 Operational Amplifier, Type 6.368 coupled with two Amplifier Networks, Type 12.782.

Figure 2:
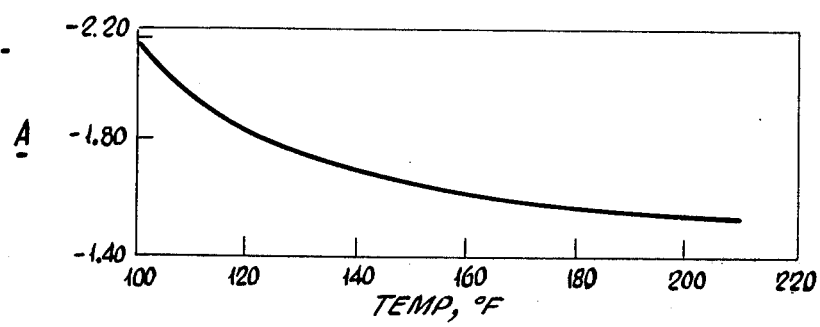
FIGS. 2 through 6, inclusive, are graphs of the quantities A, B, C, R, and W, respectively, plotted against the temperature of the hydrocarbon stream.

It will be observed that another of the three input signals to the analog addition device 37 is the product signal from the analog multiplication device 20, i.e., C ln ln $(V/S_1)$, and the third input signal is the constant A which is selected from the curve of FIG. 2. That constant is represented by a setting on a potentiometer 40.

It can be seen that the output signal from the analog addition device 37 corresponds to the Watson-Nelson characterization factor, K, in accordance with equation (2) above. This signal is, in turn, carried to a suitable display device 43, such as a chart recorder or a display meter, where the signal can be observed or recorded. The characterization factor signal can also be transmitted to upstream processing units as indicated by an output arrow 45, where it can be utilized to perform control functions such as the automatic segregation of the products of crude distillation for selected uses.

It will be clear by comparison with my prior patent, noted above, that this invention provides a method for generating a signal representative of the Watson-Nelson characterization factor which is greatly simplified. This invention needs only eight analog computing elements as compared to fourteen in my prior patent.

It can be appreciated by those skilled in the art that while electrical analog computing elements have been described, equivalent computation elements can be used, such as those of the pneumatic type, resulting in an equivalently operable system. It can also be appreciated by those skilled in the art that a digital computer can be utilized to perform the various computation steps. In the latter case the values of the constants A, B, C, R and W would be preprogrammed in the computer, or the information of the curves of FIGS. 2 through 6 would be pre-programmed, and information of the hydrocarbon temperature would be made available to the computer. Also, the sensing instruments 11 and 13 would be adapted to provide their respective signals in digital format. The advantage of the use of a digital computer lies, of course, in its accuracy and speed.

While the invention has been described with a certain degree of particularity, it can, nevertheless, be seen by the examples hereinabove set forth, that many modifications and variations of the invention can be made without departing from the spirit and scope thereof.

I claim:

1. Apparatus for generating a signal representative of the Watson-Nelson characterization factor of a hydrocarbon mixture from a source thereof wherein said mixture is at a temperature in the range of about 100° F. to about 210° F., comprising:
   (a) first means operatively coupled with said source of said hydrocarbon mixture for sensing a physical property thereof representative of the absolute viscosity thereof and for providing a first signal representative of said absolute viscosity;
   (b) second means operatively coupled with said source of hydrocarbon mixture for sensing a physical property thereof representative of of the specific gravity thereof and for providing a second signal representative of said specific gravity; and
   (c) third means operatively coupled with said first and second means for combining said first and second signals to provide a third signal representative of said characterization factor, said combining means including computing means for combining said first and second signals substantially in accordance with the following equation:

$$K = A + B/S_2 + C \ln \ln (V/S_1)$$

where:

K = the Watson-Nelson characterization factor of said hydrocarbon mixture,

V = the absolute viscosity of said hydrocarbon mixture, $S_1$ = the specific gravity at the temperature of said hydrocarbon mixture, $S_2$ = the specific gravity of said hydrocarbon mixture adjusted to sixty degrees F., and A, B and C are predetermined constants related to the temperature of said hydrocarbon mixture.

* * * * *